United States Patent [19]

Sidman

[11] 4,351,337

[45] Sep. 28, 1982

[54] BIODEGRADABLE, IMPLANTABLE DRUG DELIVERY DEVICE, AND PROCESS FOR PREPARING AND USING THE SAME

[75] Inventor: Kenneth R. Sidman, Wayland, Mass.

[73] Assignee: Arthur D. Little, Inc., Cambridge, Mass.

[21] Appl. No.: 186,152

[22] Filed: Sep. 11, 1980

Related U.S. Application Data

[63] Continuation of Ser. No. 596,444, Jul. 16, 1975, abandoned, which is a continuation-in-part of Ser. No. 361,182, May 17, 1973, abandoned.

[51] Int. Cl.³ .................................................. A61K 9/00
[52] U.S. Cl. .................................... 128/260; 128/217; 424/22
[58] Field of Search ................................ 128/260, 217

[56] References Cited

U.S. PATENT DOCUMENTS

| | | | |
|---|---|---|---|
| 923,768 | 6/1909 | Clark | 128/335.5 |
| 2,657,972 | 11/1953 | Woodward | 260/78 A |
| 3,331,814 | 7/1967 | Randall | 260/78 A |
| 3,371,069 | 2/1968 | Miyamae et al. | 260/78 A |
| 3,493,652 | 2/1970 | Hartman | 424/94 |
| 3,736,646 | 6/1973 | Schmitt et al. | 29/458 |
| 3,773,919 | 11/1973 | Boswell et al. | 128/260 |
| 3,867,520 | 2/1975 | Mori et al. | 424/36 |
| 3,887,699 | 6/1975 | Yolles | 424/19 |

Primary Examiner—V. Millin
Assistant Examiner—Nancy A. B. Swisher
Attorney, Agent, or Firm—Richard J. Hammond

[57] ABSTRACT

An implantable drug delivery device comprising a matrix formed of a poly-α-amino acid component having one or more drugs and/or diagnostic agents physically contained therein. The drug or diagnostic agent is released through one or both of two mechanisms: diffusion and biodegration which results from the action of enzymes, present in the host in which the implant is placed, on the polymeric matrix material. The implant device may be designed to release the drug or drugs at predetermined rates and in predetermined sequence. One preferred configuration for the implant device is a rod which may be inserted with a trocar.

38 Claims, 11 Drawing Figures

BIODEGRADABLE, IMPLANTABLE DRUG DELIVERY DEVICE, AND PROCESS FOR PREPARING AND USING THE SAME

This application is a continuation of application Ser. No. 596,444, filed July 16, 1975, now abandoned which is a continuation-in-part of my application Ser. No. 361,182 filed May 17, 1973, now abandoned.

This invention relates to a new form of pharmaceutical preparation and more particularly to a biodegradable implant adapted to be located within a specified region or organ of the body of a living organism for releasing one or more substances (e.g., drugs or diagnostic agents) at a controlled rate for localized or systemic utilization.

BACKGROUND OF THE INVENTION

In the administration of drugs and in the diagnosis of certain pathological conditions it is highly desirable, if not necessary, to effect a controlled release of one or more substances within the living organism, in particular within a mammalian host. For example, the controlled release of drugs (a term used hereinafter to include all substances which effect some biological response) over a period of time within a specified region or organ of the body can be used as a continuous dose, long-term delivery system for such agents as antibiotics, cardioactive medicaments, narcotic antagonists, hypoglycemic agents, fertility control agents, and the like. Likewise, the implantation of a diagnostic substance such as a dye can be used to monitor the presence or absence of a pathological condition. Devices for administering such a controlled release of drugs are generally referred to as "depots or implants", the latter term being used throughout the following description and claims.

1. Field of the Invention

Continuous, long term drug delivery devices have distinct advantages over oral administration or direct injection of drugs since neither of these earlier developed modes can achieve a desired blood level of a drug in circulation for an extended period of time. Oral administration or direct injection bring about a pulse entry of the drug which may create drug concentrations beyond the capacity of the active centers to accept the drug, and may also exceed the capacity of the metabolic and excretory mechanism of the living organism. Thus, if the level of the drug remains elevated, tissues and/or organs may sustain detrimental effects. One technique for reducing excessive concentrations has been to modify the drug structure to provide a longer metabolic half-life; but this in turn has frequently demonstrated lowered therapeutic effectiveness.

To avoid the disadvantages of oral or direct injection administration of drugs, a number of modes of administration of continuous dose, long-term delivery devices have been used or proposed. These include devices based upon ingestion, injection, vaginal and uterine insertion, percutaneous application (see for example, U.S. Pat. Nos. 3,598,122 and 3,598,123) and subcutaneous implantation. While all of these routes of administration may be found useful under one set of circumstances or the other, the use of subcutaneous implants offers a particularly desirable combination of properties to permit the administration of substances on a localized or systemic basis. To this end, subcutaneous implants serving as depots capable of slow release of a drug have been proposed. These implants suggest the possibility of attaining continuous administration over a prolonged period of time to achieve a relatively uniform delivery rate and, if desired, a static blood level. Since an excessive concentration of drug never enters the body fluids, problems of pulse entry are overcome and metabolic half-life is not a factor of controlling importance.

Despite the advantages of administering drugs from implants, prior art devices designed for this purpose have possessed one or more disadvantages which limit their acceptability and efficacy. Among such disadvantages are nonbiodegradability which may require a surgical procedure to remove them; nonbiocompatibility which may result in the introduction of undesirable and even harmful substances into the body; antigenicity which gives rise to the production of unwanted antigen bodies in the system; and difficulty in controlling release rates of the drugs.

2. Description of the Prior Art

In the prior art, a number of matrix materials and several different structural designs have been proposed for subcutaneous implants. Such materials as hydrogels, gelatin, carboxymethyl cellulose, organopolysiloxane rubbers, polyurethanes, waxes, polyvinyl alcohol, polyglycolic acid, and polylactic acid have been suggested for this purpose.

Those matrix materials, such as carboxymethyl cellulose and polyvinyl alcohol, which are water-soluble are unsatisfactory because it is not possible to control the drug release rate from them over any appreciable length of time. Those matrix materials, such as hydrogels, gelatin and collagens, which are water-swellable provide inherently rapid drug release because of their inability to retain the drug in a swelled condition. Moreover, a material such as gelatin has an extremely complex chemical structure formed of some twenty amino acids and there appears to be no satisfactory way to control or adjust its physical properties for use as an implant matrix. Collagen-based implants are described in the literature (see for example Rubin et al "Collagen as a Vehicle for Drug Delivery", *The Journal of Clinical Pharmacology*, August-September, 1973, pp. 309–312.)

More recently, absorable, biocompatible matrix materials formed of polyglycolic acids, polylactic acids or mixtures of these have been disclosed. (See for example U.S. Pat. No. 3,773,919 and reports on Contract DADA-17-72-C-2079 to Dynatech Research and Development Co., with U.S. Army Medical Research and Development Command, Washington D.C. (1972).) These delivery devices consist of a polymer matrix in which the drug is physically entrapped. The drug is released, not by diffusing through a polymeric membrane, but by hydrolytic breakdown of the polymer matrix itself. As the polymeric matrix disintegrates, the enclosed drug is released into the surrounding body fluids. By the time all of the drug has been released from the matrix, the polymer fragments have been almost completely absorbed. Although these matrix materials make it possible to provide biodegradable and biocompatible implant devices having less rapid release rates, they present serious problems in the accurate control of release rates. These problems in release rate control arise because the polylactic acids and polyglycolic acids in degradation break down to form lactic acid and glycolic acid. Degradation is the result of hydrolysis which is dependent upon both pH and degree of crystallinity of the polymers. Since the products of these hydrolysis reactions are acids, there is a tendency for the products that do not immediately diffuse away from the implant site to accelerate further hydrolysis. In addition, the crystalline regions degrade at a much slower rate than the amorphorus regions, thus giving rise to a nonuniform degradation pattern and a porous structure from which the drugs may be released at an uncontrollable rate.

Organopolysiloxane rubbers as carriers for the controlled release of drugs have received widespread attention. The use of such materials in implant devices is described in U.S. Pat. Nos. 3,279,996 and 3,518,340. Implants which use any of these materials as substrates or carriers which are not absorbable by the living organism into which they are introduced normally require removal by surgery. The silicone rubbers are among the nonabsorbable materials and therefore they suffer from this drawback. Typically, implants formed of silicone rubber, or of any of the other above-named materials, have been fabricated either in the form of closed hollow tubes or capsules (with or without a sponge sleeve) in which the drug is contained for diffusion through the tube walls; or they have been made up into structures of homogeneous polymer-drug blends. Another type of subcutaneous implant which requires removal is described in U.S. Pat. No. 2,625,158.

Some work has been reported on implants formed by chemically bonding drugs to polypeptides (see for example Jablon, P. A. M., Ph.D. Thesis, Purdue University, 1969). This approach necessitates providing a drug having a reactive site amenable to chemical bonding to the polypeptide; and it also introduces the danger that in the breaking of the chemical bond to release the drug the effectiveness and acceptability of the drug to the system may be materially altered. Moreover, the drug-polypeptide complex will, in fact, represent a new drug of unknown properties. Finally, an implant in which the drug is chemically bonded to the matrix material can not release the drug from the matrix by the process of diffusion, since release is predicated on the actual breaking of chemical bonds.

U.S. Pat. No. 3,493,652 teaches the incorporation of medicaments such as cardioactive, adrenergic, cholinergic, antispasmodic and curariform agents, tranquilizers, antihistamines, antibiotics and the like into a matrix which contains one or more enzymes or enzyme precursors capable of digesting the matrix material which, in turn, may be formed of such diverse materials as casein, fibrinogen, proteins, polypeptides with free amino groups, urea and amino acids. The dosage formulation may take many different forms including suspensions, emulsions, tablets (sublingical, buccal, oral or vaginal), capsules, ointments, suppositories and implants. When such a controlled release medicament is introduced into a living organism it must, of necessity, introduce both the substrate material and enzyme into the system and one or both of these may be antagonistic to the system. In particular, to introduce those enzymes which are not normally present in the living organism may result in harmful side effects. Moreover, enzymes are known to degrade or denature and this process may take place prior or subsequent to the administration of the dosage. In the first case, the effectiveness of the dosage-contained enzyme is lessened or even cancelled; and in the second case, premature enzyme degradation could materially alter or even destroy any control over the drug release rate.

A field which is somewhat related to implants is that concerned with sutures. Prior art in this field teaches, among many variations, the incorporation of antiseptics into sutures derived from animal tissue (U.S. Pat. Nos. 923,768 and 1,382,715); sutures of proteins or other nitrogenous amphoteric organic materials having a germacide chemically bonded thereto (U.S. Pat. No. 3,642,003); and sutures formed of or incorporating polymers and/or copolymers of glycolic acid and lactic acid (U.S. Pat. Nos. 3,636,956 and 3,736,646). Finally, the prior art discloses biodegradable sutures formed of a copolymer of glycolic and lactic acids (U.S. Pat. No. 3,736,646) and of a polylactide polymer or copolymer (U.S. Pat. No. 3,636,956).

Inasmuch as the matrix materials of the implant devices of this invention are polypeptides, i.e., poly-$\alpha$-amino acids, the prior art disclosing the use of polypeptides in therapeutic devices also deserves attention. Such prior art includes sutures made of copolypeptides (U.S. Pat. No. 3,371,069); wound dressings formed of a polypeptide film containing a therapeutic agent and a carrier which transports the therapeutic agent to the dressing surface (U.S. Pat. No. 3,867,520) and dressings for burn wounds formed of a nylon velour fabric laminated with a synthetic polypeptide material designed to cover burns to provide a framework into which fibroblastic proliferation could occur (Spira et al "Evaluation of Synthetic Fabrics as Artificial Skin Grafts to Experimental Burn Wounds" *J. Biomed. Mater. Res.,* 3: 213–234 (1969) and Walder et al "Evaluation of Synthetic Films as Wound Covers" *Trans. Amer. Soc. Artif. Int. Organs,* 15: 29–32 (1969).)

It will thus be apparent from this discussion of the prior art that implants for controlled drug release have distinct theoretical advantages; but that there is a need for an improved implant device to achieve a continuous dose, controlled release of drugs or other substances which overcome the major disadvantages (i.e., difficulty in continuously controlling the release of the drugs, production of unwanted degradation products and/or the need for surgically removing the implanted matrix) associated with the presently available implant devices.

OBJECTS OF THE INVENTION

It is therefore a primary object of this invention to provide an improved implant device for achieving continuous dose, controlled-release of drugs or other substances such as diagnostic agents. It is a further object of this invention to provide an implant device of the character described which may be biocompatible and biodegradable to form amino acids and/or amino acid complexes already present in the organism into which the implant is placed, thus eliminating the introduction of foreign or antagonistic substances and at the same time eliminating the need of surgical procedures to remove a matrix sturcture. An additional object of this invention is to provide an improved implant device which exhibits improved release rate control, the rate of release being optionally constant or at some predetermined changing rate. Another object is to provide an implant device which may rely upon one or more enzymes normally present in the living organism to release one or more drugs continuously, or upon one or more enzymes which are only present under certain pathological conditions to release one or more drugs and/or diagnostic indicators when such pathological conditions are present. It is yet a further object of this invention to provide an improved implant device which may be used to deliver a wide range of drugs or other agents, including two or more drugs simultaneously or serially.

It is another primary object of this invention to provide a process for forming a biodegradable implant devices in various configurations to attain controlled drug release at a constant or varying release rate and to attain the release of two or more drugs either simultaneously or serially. Another object of this invention is to provide a process of the character described which is amenable to the formation of an implant device to deliver a wide range of drugs and other substances such as diagnostic agents.

Still another primary object of this invention is to provide an improved process for the continuous, rate-controlled delivery of drugs and/or other substances into selected areas or organs of living organisms in a manner to minimize or eliminate the introduction of any substance, other than the drug or other agent, not normally present in the organism.

Other objects of the invention will in part be obvious and will in part be apparent hereinafter.

SUMMARY OF THE INVENTION

The implant device of this invention, which is designed for controllable release of a substance into a living organism and particularly into a mammalian host, comprises a biocompatible, biodegradable poly-α-amino acid structure containing the substance to be released. Release of the substance may be through diffusion, hydrolysis of the polymer or a combination of both of these mechanisms. The poly-α-amino acid, which is a synthetic polymer composed of α-amino acid residues linked by peptide bonds, is degradable through the action of one or more enzymes which are provided by the body fluid, tissue or organ of the host within the area of the implant. The degradation products, i.e., amino acids, are metabolized or excreted by the organism during and/or after release of the substance. The implant may be in the form of a film, rod, fiber, hollow cylinder, closed tube, microcapsule, microchip, and the like; and it may have the drug so distributed as to provide a constant or a changing rate of release. The poly-α-amino acid may be a homopolymer or a copolymer of two or more amino acids; and it may be chosen as to be biodegradable through action of one or more enzymes which are normally present in the living organism or through action of one or more enzymes developed by a pathological condition thus effecting the triggering of the release only upon certain predetermined conditions.

The biodegradable implant of this invention may be formed by one of several different techniques. If the implant comprises a matrix structure in which the drug to be released is distributed throughout in the desired concentration, it is preferred to physically incorporate the substance into the poly-α-amino acid matrix and then shape the implant structure by casting from a solution, by injection molding, by extruding or by other suitable processes. If the implant takes the form of a closed tube, the outside of which is formed of the poly-α-amino acid without any drug, then a drug-containing core may be formed and coated with the polymer or inserted into a polymer shell. Likewise, microcapsules may be formed by well-known coating or microencapsulation techniques.

Although it may be preferrable in practicing one or more of these techniques of implant manufacture to add processing aids such as solvents, plasticizers and the like, such processing aids do not alter or effect the release of the drug from the implant once the implant is placed at the release site and begins to deliver the drug.

The implant is introduced within the living organism by any suitable technique.

The invention accordingly comprises the several steps and the relation of one or more of such steps with respect to each of the others, and the article possessing the features, properties and the relation of elements, which are exemplified in the following detailed disclosure, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which.

DETAILED DESCRIPTION OF THE INVENTION

The biocompatible, biodegradable implant device of this invention is formed as a structure in which the drug or other releasable substance to be delivered is physically contained by a poly-α-amino acid. In the following description and claims the term "drug" is used in its broadest sense and it includes any substance which has any biological activity, whether such activity is medicinal or otherwise. For convenience in presenting this detailed description, the implant will be described in terms of containing a drug, although it is to be understood that it may also contain a diagnostic agent such as a releasable dye which has no biological activity per se. Thus, in its broadest sense, the implant may be defined as containing a releasable substance, which may or may not exhibit biological activity.

The polymer, in which the drug is contained for release, is one or more poly-α-amino acids having low toxicity and being biodegradable in vivo through enzymatic hydrolysis to form amino acids. The poly-α-amino acids may be further generally characterized as polymers which do not form covalent bonds with the drugs they contain and which are soluble in selected solvents.

Poly-α-amino acids are synthetic polymers composed of α-amino acid residues linked by peptide bonds. They have been extensively studied, particularly with relation to the structure of the polypetide chain and its susceptibility to hydrolysis by proteolytic enzymes (see for example C. H. Bamford, A. Elliott and W. E. Hanby, "Synthetic Polypeptides," Academic Press Inc., New York, 1956, pp. 113-425). The biological properties of polypeptides have also been extensively investigated (see for example M. A. Stahman, Ed., "Polyamino Acids, Polypeptides, and Proteins," The University of Wisconsin, 1962, Part V, pp 283-385).

Synthetic techniques have been developed for forming homopolymers, random copolymers, block copolymers, multi-chain polymers and polymers containing a predetermined sequence of amino acid residues from α-amino acids. (See for example U.S. Pat. Nos. 2,657,972 and 3,331,814).

Homopolymeric poly-α-amino acids may be represented as wherein $R_1$ is a side chain characteristic of the common, well-known amino acids, including, but not limited to and the like.

The poly-α-amino acid copolymers are composed of two or more α-amino acids which may be distributed at random along the polymer chain; and such polymers can be represented, as for example, as where $R_1$ and $R_2$ are different and are chosen from the groupings given above for $R_1$.

Block copolymers are also known and may be represented generally as where $R_1$, $R_2$, $R_3$, $R_4$, etc., may be the same or different and are chosen from the grouping given previously for $R_1$; and m, n, p, q, etc., range generally between one and one hundred. The poly-α-amino acids may be synthesized to have a wide range of molecular weights, e.g., from $10^3$ to $10^6$; and when used in the implant devices of this invention, mixtures of polymers of different molecular weights may be employed.

Multichain (nonlinear) polypeptides are produced through the chemical attachment of individual amino acids or low molecular weight polypeptides (e.g., a molecular weight of less than about 10,000) to a linear polypeptide that serves as the backbone.

Although a number of derivatives of α-amino acids and peptides have been used as monomers for the preparation of the poly-α-amino acids, the most commonly used monomers are the N-carboxy-α-amino acid anhydrides represented as where R is chosen from the same groupings as given for $R_1$ above. The polymerization technique may be either the well-known bulk or solution polymerization process. Bulk polymerization is usually carried out at elevated temperatures and yields polymers with relatively low average molecular weights. Solution polymerization, on the other hand, may be performed at low temperatures, it is easily controlled and can result in relatively high molecular weight polymers. Inert solvents such as dioxane, dimethylformamide and nitrobenzene may be used with such polymerization catalysts as primary, secondary or tertiary amines, or strong bases such as sodium methoxide or sodium hydroxide. The use of tertiary amines or sodium methoxide as initiators are preferred for the preparation of poly-α-amino acids with average molecular weights of 20,000 to 1,000,000. The primary and secondary amines have been found useful in preparing intermediate molecular weight polymers, e.g., $10^3$ to $10^4$.

Almost all of the amino acids occuring in proteins have been prepared in homopolymeric form. The following are representative amino acids which have been polymerized and solvents for the polymers

| amino acid | solvents |
| --- | --- |
| L-Alanine | dichloroacetic acid, trifluoroacetic acid |
| Glycine | dichloroacetic acid, trifluoroacetic acid, concentrated aqueous LiBr |
| L-Leucine | trifluoroacetic acid |
| L-Lysine | water |
| L-Methionine | chloroform, dichloroacetic acid |
| L-Phenylalanine | 33% HBr in glacial acetic acid |
| L-Proline | water, acetic acid |
| L-Valine | trifluoroacetic acid. |

In general, the copolymers exhibit solubility in common organic solvents such as chloroform, benzene and dioane, and they generally possess improved physical characteristics, such as improved malleability and greater elongation to break, than the homopolymers, thus making them preferable in the practice of this invention. Exemplary of such copolymers are those formed from γ-benzyl-L-glutamate and leucine following the procedure of Blout and Karlson (see J. Amer. Chem. Soc. 78, 941 (1956)). These copolymers have molecular weights in excess of 50,000 and have the desirable film forming and mechanical properties. It may also be desirable to add a minor quantity of a monomer other than an α-amino acid to contribute desired physical properties.

The poly-α-amino acids used in the implant devices of this invention must have sufficient mechanical strength to be formed into such structures as films, rods, fibers, closed tubes, hollow cylinders, microcapsules, microchips, and the like. The poly-α-amino acids must also be of a type which lend themselves to formation into such structures by known synthetic resin fabrication techniques as described below.

The poly-α-amino acids used must also possess certain other properties, foremost among which is biocompatability and biodegradability. In beging biocompatible, the polymers must be essentially nontoxic and nonantigenic. In being biodegradable, they must be capable of breaking down to form amino acids or related materials which can be assimilated within the host environment. Biodegradability is at least in part determined by the type and sequence of the amino acids forming the polymer. However, it is not required that biodegradation be completed by the time that the supply of drug being released is exhausted.

The poly-α-amino acids should also be essentially water-insoluble at the pH of the host environment. For any implant device that is to deliver a drug over an extended period of time, the poly-α-amino acid should also be sufficiently hydrophobic so that no significant swelling occurs in the host environment. Since water swellability, like biodegradability, is a function of the type of amino acids used to form the polymer, the final choice of amino acid or acids and the sequence of the acids in the polymer is made on the basis of balancing these two properties to attain the desired performance from the implant. The effect of these factors will be illustrated in the examples given.

A wide range of drugs may be incorporated into these synthetic polymer matrices to form the implant devices of this invention. Such drugs include, but are not limited to, fertility control agents such as progesterone, d-norgestrel, estradiol valerate, medroxyprogesterone acetate, and hydroxyprogesterone caproate; narcotic atagonists such as naltrexone, naloxone and diprenorphine; anticoagulants such as heparin or ethylenediaminetetraacetic acid; antibacterials; antibotics; antineoplastic agents; cardiovascular agents such as digitalis, quinidine and nitroglycerine; immunological agents; central nervous system stimulants and depressants; antidiabetic agents, and the like. Diagnostic agents such as dyes (e.g., bromsulphalein) may be incorporated for implantation at a site where enzymes, formed as a result of a pathological condition to be detected, are available for the hydrolysis of the matrix material. The release of such diagnostic agents brought about by the presence of the pathologically-induced enzyme may be detected in the body fluids, e.g., the urine, to indicate the presence of the pathological condition being monitored.

The quantity of the drug or drugs or of diagnostic agent incorporated into the poly-α-amino acid matrix will depend upon the rate and the length of time over which it is to be released, which in turn will depend upon the diffusion rate of the drug and upon the rate at which the polymeric matrix is hydrolyzed by one or more enzymes. Actual continuous dosage rates may be determined in vivo using the enzymes to be encounted in vivo in the biodegradation of the matrix polymer with the release of the drug or diagnotic agent contained.

As previously noted, the implant device of this invention may take one of several forms. In those forms where the drug to be delivered is distributed throughout the poly-α-amino acid serving as a matrix, the drug (or diagnostic agent) is blended with the polymeric matrix material and then the resulting physical mixture is fabricated into the desired structural shape.

Figure 1:
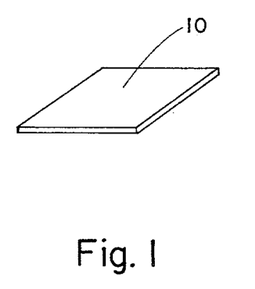
FIG. 1 illustrates an essentially "two-dimensional" implant device particularly suitable for in vivo testing.

Such blending may be done by one of several techniques. The first of these comprises forming a solution of the polymeric matrix material and adding the drug to the solution. If the solvent or solvent mixture used to form the solution of the matrix is also a solvent for the drug, then a homogeneous solution may be formed. If the solvent system is not a solvent for the drug, then the drug may be dispersed as fine particulate material, as a liquid, or in other suitable form, throughout the polymer solution using, if necessary, a high-shear mixer to obtain a homogeneous suspension. The solution or suspension thus formed may be cast into films or ribbons such as illustrated in FIG. 1 which illustrates an implant 10 having essentially but two dimensions, width and length. Solvent and casting conditions are chosen to prevent any appreciable segregation of the drug and polymer when the solvent is removed. The flat, essentially two-dimensional implant 10 of FIG. 1 exhibits a relatively constant surface area over its useful life within a living organism and hence it may be used to administer a relatively constant dose rate. The film or ribbon form of implant is not, however, particularly amenable to administration by trocar, a fact which means that surgical implantation procedures may be required. This form of implant has, however, been found convenient for making in vivo and in vitro evaluations of a large number of drug-polymer combinations and it serves well as a model delivery system for such evaluation work.

Another blending technique may comprise mixing the drug with the dry polymeric matrix material in powdered form and then forming the desired structural shape with heat and pressure, the fabrication conditions being such as not to destroy the efficacy of the drug or to degrade the matrix material. The blend of drug and dry polymeric matrix material may be injection molded, compression molded or extruded into three-dimensional shapes of a required design.

Under some circumstances it may be necessary or desirable to add a processing aid in forming three-dimensional implant configurations such as illustrated in FIGS. 2-7. Such processing aids may include, but are not limited to, solvents, plasticizers, and the like. However, in no case does such a processing aid serve as a drug carrier in that it "blooms" or moves to the implant surface transporting the drug with it during the use of the implant within the host environment.

Figure 2:
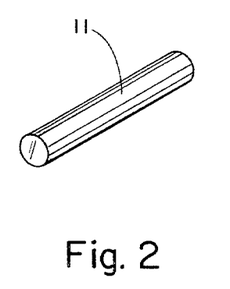
FIG. 2 illustrates an implant device constructed in accordance with this invention in the form of a rod.

Extrusion of such a blend may be used to form fibers or rods such as shown in FIG. 2 which illustrates a solid rod-shaped implant 11. In an implant device of this form in which the drug is released essentially solely through the mechanism of biodegradation brought about by the action of one or more enzymes present in the host environment then such biodegradation will expose a constantly decreasing surface area and hence will release the drug at a decreasing rate. Moreover, this change in rate may be altered if drug delivery from the implant is brought about principally or coincidentally by diffusion. No matter what the mechanism of drug delivery is, however, the rod- or fiber-shaped implant of FIG. 2 may be used without further modification. Thus the implant devices of this invention function without the incorporation of any added drug carriers.

Figure 3:
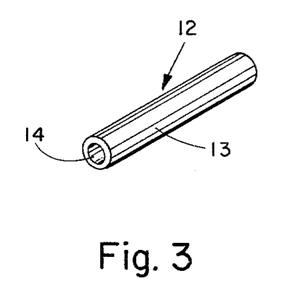
FIG. 3 illustrates an implant device in the form of a hollow cylinder.
Figure 4:
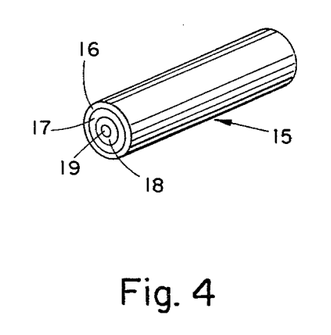
FIG. 4 illustrates an implant device in the form of a layered rod in which the drug concentration is different from its adjacent layer or layers to achieve a predetermined rate of drug release.
Figure 5:
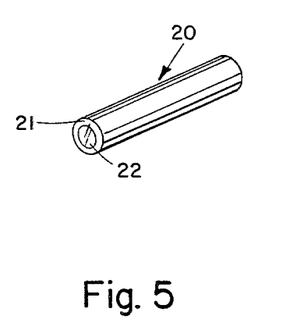
FIG. 5 illustrates an implant device in the form of a rod with a core containing a drug different from the surrounding layer.

Since a rod- or fiber-shaped implant is desirable for administration by means of a trocar, it may be desirable to modify this implant configuration to obtain a drug release rate different from that obtained through the use of the unmodified rod structure of FIG. 2. Thus the implant may be designed to achieve an essentially constant rate of drug release or a rate which does not decrease as rapidly as the implant 11 of FIG. 2. FIGS. 3 and 4 illustrate two exemplary modifications of a rod-shaped implant. In FIG. 3 the implant 12 is constructed as an open cylinder having an external surface 13 and axial opening defining an internal surface 14. Since the surface area of external surface 13 will decrease and that of internal surface 14 will increase as the implant is degraded, the rate of drug release may be held constant, or it may be increasing or decreasing depending upon the relative rate at which the surface areas of surfaces 13 and 14 decrease and increase. As in the case of the implant of FIG. 2, the release of the drug by diffusion in addition to or primarily in place of polymer degradation will affect the delivery rate. However, by providing the added internal surface in the configuration of FIG. 3, release rates may be further controlled irrespective of the mechanism by which the drug is delivered to the host system.

In the modification of FIG. 4, the implant device 15 is formed of multiple layers as exemplified by layers 16, 17, 18 and 19, the last serving as a core. In this implant, each layer may have drug concentration different from that of an adjacent layer or layers. If these drug concentrations are arranged to provide a concentration gradient which increases from the outermost layer 16 to core 19, a constant drug release device may be formed in rod form. In forming the rod implant 15 of FIG. 4, the multiple layers may be coextruded using well developed techniques. If desired, the concentration gradient profile from the rod center to its external surface may be smoothed by annealing the extrudate at a temperature slightly below the melt temperature of the polymeric matrix material so that thermal diffusion of the drug is effected. An alternative procedure for forming the multilayered implant with a drug concentration gradient is to form a core and coat it with successive layers of a polymeric matrix solution containing the drug dissolved or dispersed therein. It is, of course, also within the scope of this invention to form a multilayered implant such as 15 of FIG. 4 by a combination of techniques, e.g., extrusion and coating; and to make multilayered implants wherein the drug concentration as well as the poly-α-amino acid matrix differs from layer to layer.

Under some circumstances, it may be desirable to release two different substances in series. For example, in the implant 20 of FIG. 5, the outer layer 21 may contain a first anticancer drug which is to be delivered up to its toxic level and core 22 may contain a second anticancer drug which is then delivered subsequent to the attainment of the toxic level of the first drug. Likewise, the implant device of FIG. 5 may be formed to contain in outer layer 21 a diagnostic agent which, when released through action of a pathologically-developed enzyme, will indicate an abnormal situation and then after giving such warning will release one or more drugs from core 22. The implant embodiments of FIGS. 4 and 5 may also be used to release more toxic drugs or more toxic dosages if the system does not respond to the first drug or dosage released.

Figure 6:
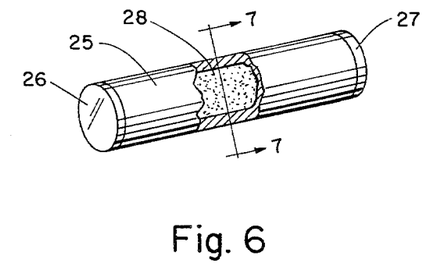
FIG. 6 illustrates an implant device of a rod configuration which is a closed tube containing all, or most, of the drug within the tube.
Figure 7:
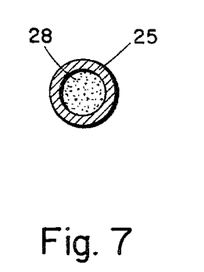
FIG. 7 is a transverse cross section of the closed tube of FIG. 6 taken through plane 7—7 of FIG. 6.

FIGS. 6 and 7 illustrate another modification of a rod-shaped implant device constructed in accordance with this invention. This modification is a closed tube and it comprises a cylindrical casing 25 formed of a poly-α-amino acid. Casing 25 is closed at both ends, for example by end caps 26 and 27 also formed of polymer. Within the tube there is a core 28 which may be formed only of the one or more drugs to be delivered. Core 28 is, however, preferably formed of the drug or drugs distributed throughout a matrix of a suitable poly-α-amino acid, the drug loading in core 28 generally being relatively high.

The closed tube modification of the rod-configured implant device may be formed by any one of a number of suitable techniques. For example, if the core is made up of drug only, the casing may be extruded, filled with drug and then capped. Alternatively, the drug core may be formed and then coated with a polymer solution by spraying, dipping, and the like. If the core is formed of the drug in a polymer matrix, the components may be blended and shaped as previously described. Such a core may be slipped into a suitably-sized preformed casing which is then capped, or it may be coated with a polymer solution. The core and casing may also be coextruded, cut into desired lengths and then capped. Thus this form of implant device lends itself to a wide variety of manufacturing techniques, all within well-developed skills.

Although the polymer used to form the casing around the core will normally be the same as that used as the matrix for the core, this is not necessary; and in some instances the use of two different polymers may be desirable to obtain an even more exacting control over drug delivery.

The closed tube modification of the rod-configured implant device constructed in accordance with this invention has several advantages. One very important advantage is the possibility of attaining drug loadings as high as 80% to 90% by weight thus allowing a minimum overall size of depot and requiring a minimum amount of polymer to be removed by biodegradation. Another advantage lies in the fact that implant devices in the form of a closed tube may exhibit a constant rate of drug release, primarily by diffusion, and hence achieve a high utilization of the drug payload. Also, being of a rod-configuration, these closed tubes may be administered by trocar injection, thus eliminating any surgical procedure.

Figure 8:
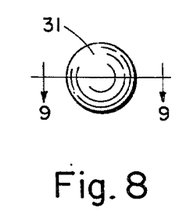
FIG. 8 shows a microcapsule implant constructed in accordance with this invention.
Figure 9:
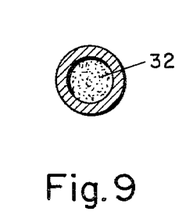
FIG. 9 is a cross section through the microcapsule of FIG. 8 taken through plane 9—9 of FIG. 8.

FIGS. 8 and 9 illustrate yet another configuration which the implant device of this invention may assume, namely as a microcapsule. The microcapsule 30 has an outer coating 31 of only polymer and a spherical (or other similar configuration) core 32 formed, as in the case of the closed tubing of FIGS. 6 and 7, of either pure drug or of a drug/polymer blend. The microcapsule configuration can be constructed to deliver a drug at an essentially constant rate; and it may be desirable for certain drug delivery applications. For example, the use of these microcapsule implants provides one way to deliver a mixture of drugs, some implants containing one drug and some another. Any suitable technique (tumbling, dipping, spraying, coaceration or the like) may be used to form such microcapsule implant devices. It will thus be apparent that a large number of embodiments of the multilayered implant are possible to meret different needs.

The implant devices of this invention may be located in or near an organ of the body, or they may be implanted subdermally, e.g., in the forearm or sublingually. They may also be administered as uterine or vaginal inserts. The location of the implant will determine the enzymes which will be present to effect the biodegradation of the poly-α-amino acid matrix and hence will determine the composition of the matrix material. The proteolytic enzymes within the mammalian system include, among others, prolidase, prolinase, thrombin, renin, carboxypeptidase A, proline, iminopeptidase, pepsin, trypsin, chymotrypsin, leucineaminopeptidase, carboxypeptidase B, and cathepsin A, B, $B_2$, C and D.

The poly-α-amino acid drug delivery system of this invention, when implanted in the body, will be exposed to a multiplicity of proteolytic enzymes, all of which are capable of forming enzyme-substrate complexes. As noted above, the poly-α-amino acid substrate (matrix) is chosen according to the location of implant and the reactive enzymes present at that location.

The effect of selected enzymes on selected poly-α-amino acids is shown below:

| Enzyme | Poly-α-amino acid | Effect |
|---|---|---|
| Trypsin | poly-L-ornithine | resistant |
| | poly-D-lysine | resistant |
| | poly-L-lysine | hydrolyzed |
| | copol-(L-lysine: L-glutamic acid, 1:4) | resistant |
| | copol-(L-lysine: L-glutamic acid, 1:1) | sl. hydrolyzed |
| | copol-(L-lysine: L-tyrosine, 3:1) | sl. hydrolyzed |
| Chymo-trypsin | poly-L-glutamic acid | resistant |
| | poly-L-tyrosine | resistant |
| | poly-L-phenylalanine | resistant |
| | poly-L-tryptophan | resistant |
| | copol-(L-lysine: L-leucine: L-tyrosine, 2:1:1) | hydrolyzed |
| | copol-(L-glutamic acid: DL-alanine: L-tyrosine, 2:1:1) | hydrolyzed |
| | copol-(L-lysine: L-tyrosine, 2:5:1) | |
| | copol-(L-lysine: L-phenylalanine, 2:1) | hydrolyzed |
| | copol-(DL-alanine: L-tyrosine, 9:1) | resistant |
| | copol-(L-proline: L-tyrosine, 23:1) | resistant |
| Pepsin | poly-L-glutamic acid | hydrolyzed |
| | copolymers of L-glutamic acid with L-lysine, L-aspartic acid L-alanine; or L-phenylalanine | hydrolyzed |
| | poly-L-lysine | resistant |
| | poly-D-glutamic acid | resistant |
| | poly-L-aspartic acid | resistant |
| Carboxy-peptidase A | poly-L-glutamic acid | hydrolyzed |
| | poly-L-lysine | resistant |
| Proline Imino-peptidase | poly-L-proline | hydrolyzed |
| Taka-Diastase | poly-L-histidine | hydrolyzed |

The implant device, the process for its preparation, and the process for its use to attain a continuous sustained drug release are further described in the following examples which are meant to be illustrative and not limiting.

EXAMPLE 1

Implantable sustained release devices were prepared in accordance with this invention for the administration of prednisolone in laboratory rats. The polymeric matrix was a copolymer of two α-amino acids, namely γ-benzyl-L-glutamate and L-leucine (50/50 mole ratio).

The copolymer used in forming the matrix was prepared from the N-carboxy anhydrides of the α-amino acids. The procedure used in preparing the N-carboxy anhydrides was as follows. One hundred grams of the finely powdered α-amino acid was charged into a reaction flask and suspended in 600 cc of a dry, inert solvent, e.g., dioxane or tetrahydrofuran. A stream of phosgene was slowly introduced into the flask while the temperature was maintained between 40° and 60° C. This was continued until the α-amino acid was dissolved, usually about two to six hours. The straw-colored reaction mixture was concentrated in vacuo at a maximum temperature of 50° C. The resulting oil was then diluted with chloroform and n-hexane was added slowly until crystallization began. Crystallization was complete in 12 hours at 3° C. The resulting precipitate was isolated by filtration, was thoroughly washed with n-hexane to remove excess phosgene and then recrystallized from a chloroform solution.

The melting point of the N-carboxy anhydride of γ-benzyl-L-glutamate thus prepared was 93°–94° C. and that of the N-carboxy anhydride of L-leucine was 76°–77° C.

The copolymerization of the two N-carboxy anhydrides was carried out following the procedure of Blout and Karlson (J. Amer. Chem. Soc. 78 941–46 (1956)). Dioxane was used as the solvent and it was added at a level of 1–4 ml/millimole of the N-carboxy anhydrides.

To prepare the 50/50 mole ratio copolymer equal moles of the two N-carboxy anhydrides were charged into a dry reaction flask. Sufficient dioxane was added to produce a 5% by weight solution of the N-carboxy anhydrides in the solvent. Dry triethylamine was used as the polymerization catalyst at a level of one part by weight catalyst to 200 parts of the N-carboxy anhydrides.

The flask was stoppered and allowed to stand at room temperature for 120 hours. The reaction solution was then poured with vigorous stirring into 95% ethanol to precipitate the copolymer. It was recovered by filtering. The copolymer was recrystallized from dioxane using 95% ethanol as the nonsolvent until the resulting copolymer had a melting point range of 225° to 235° C. (typically requiring about four recrystallizations).

A drug delivery implant device in thin film form was prepared using this copolymer as the polymeric matrix and prednisolone as the drug.

To 100 cc of dioxane were added 1.5 g of the copolymer and 0.15 g of prednisolone (ICI, Nutritional Biochemicals) and 0.002 mg (specific activity, 45.5 curies/mM, in 0.5 cc of a benzene/ethanol (9/1) solution) of tritium-labelled prednisolone (New England Nuclear, Boston, Mass.). This mixture was gently stirred for 16 hours to obtain a homogeneous solution.

The solution containing the copolymer and the drug was cast on a level glass plate that had been covered with a fluoropolymer release film; and the solution was spread with a draw down bar to give a uniform thickness of 30 mils.

The solvent in the coating was allowed to evaporate under the heat from a heat lamp until the film because nontacky. This required about two hours. At this point another layer of copolymer/drug solution was cast on the first film, drawn down to give a thickness of 30 mils and dried as before. A total of seven film layers were thus built up in this manner to give a film with a final thickness of 0.4 mil.

Scanning electron microscope pictures (2000x) of the surfaces and of cross section of the film showed no evidence of separate drug and copolymer phases, thus indicating that a very fine dispersion of the drug had been achieved.

Implants were prepared from the film by cutting it into rectangular pieces that exhibited various surface areas. These implants contained from 0.65 to 2.0 mg of radioactively-labelled prednisolone, depending on the size of the implant rectangle. The implants were sterilized by immersion in alcohol and then rinsed with sterile Earle's Balanced Salt Solution. The devices were implanted subcutaneously into the backs of two groups each of eight female CD rats (Charles River Breeding Laboratories, Inc.). To accomplish the implantations, the dorsal area was shaved, cleaned with alcohol and then a one-half inch incision was made in the skin. The skin was then separated from the muscle tissue and the implant inserted at this site. The incision was then sutured.

Each animal of a third group of four female CD rats from the same source was subcutaneously injected with 0.5 cc of an 0.5% hydroxy propylcellulose solution containing an amount of the same radioactiviely labelled prednisolone approximately equivalent to that contained in the implant devices (i.e., 1 mg prednisolone/rat).

All of the animals were housed in metabolic cages. The radioactivities in the urines collected were measured by the standard procedure of scintillation counting, and from these measurements values of disintegrations per minute (DPM) were calculated. Radioactivities were thus measured every 24 hours for the first four days and then for an additional 72 hour level to complete a week of testing.

The average DPM values obtained for the two groups of implanted rats (average dosage of 1.5 mg/rat) and the one group of control rats (average dosage of 1.0 mg/rat) are given in Table 1. During the first day a number of rats escaped from their cages so that the average figures given are for fewer than the total number of animals in each group.

TABLE 1

| Group No. | Tritium (DPM) in Urine of Rats Time Span, Hours | | | | |
|---|---|---|---|---|---|
| | 0–24 | 24–48 | 48–72 | 72–96 | 96–168 |
| 1-Implanted | 11,006* | 5,272+ | 3,425 | 2,415 | 3,705 |
| 2-Implanted | 8,529 | 5,693 | 3,972 | 2,668 | 3,968 |
| 3-Control | 33,038 | 4,424 | 3,335 | 86 | −248 |

*Average of two;  average of 6;  average of 3;  +average of 7

From Table 1 it will be seen that the control animals exhibited very high excretion rates in the first 24 hours and that by the end of the fourth day there was practically no excretion of radioactive material. The presence of minus values in these readings indicates that there was some unidentified "noise" in the system. However, this does not detract from the conclusions which may be drawn from these data. It will be seen that the level of excretion of radioactive material released by the implant devices was considerably lower initially than when the drug was injected subcutaneously. However, the drug was released from the implants at an essentially sustained rate and all of the animals were still showing significant levels of radioactivity (and hence drug release) in their urine at the end of one week.

EXAMPLE 2

The N-carboxy anhydride of γ-benzyl-L-glutamate and the N-carboxy anhydride of L-leucine were prepared in the same manner as described in Example 1. From these were formed copolymers of benzyl glutamate/leucine (40/60 molar ratio) and of glutamic acid/leucine (40/60, 35/65, 20/80 and 10/90).

The general procedure for forming these copolymers was as follows: A 2% solution of the monomers at the appropriate molar ratio was prepared in benzene or dioxane in a three-neck flask with mechanical stirrer, condenser, and a calcium chloride drying tower. An atmosphere of nitrogen was maintained at the condenser exit. The initiator solution (triethylamine in either benzene or dioxane in a concentration of 0.102 N) was added in the required amount by syringe and the clear, colorless solution was stirred for four to seven days. In the formation of the benzyl glutamate/leucine copolymer, the reaction solution was poured into 95% ethanol to precipitate the copolymer. After recovery by filtration the copolymer was recrystallized from dioxane using 95% ethanol.

In preparing the glutamic acid/leucine copolymer, it was necessary to remove the protective benzyl groups. This was accomplished as follows: In those runs where benzene was used as a solvent, debenzylation of the polymer was carried out by treatment with anhydrous hydrogen chloride for 40–60 minutes, followed by anhydrous hydrogen bromide until precipitation of the polymer was complete. The mixture was purged vigorously with nitrogen to remove excess HBr, and then filtered under nitrogen pressure. The polymer was washed with fresh benzene, transferred to a Soxhlet, and extracted with refluxinng ether to remove traces of color. The extraction was carried out for one-to-three days. The polymer was then air dried.

Where dioxane was used as the solvent, the reaction solution, at the end of the polymerization period, was poured into excess 95% alcohol, and the colorless, fibrous polymer was filtered under vacuum. After drying in the oven at 40° C., the product was dissolved in benzene, and a portion of solvent was distilled at atmospheric pressure to remove traces of alcohol and water. The solution was allowed to cool to room temperature and debenzylation with HCl and HBr was carried out as described above.

In preparing films to be cut into implants for in vivo evaluations, solutions (from about 1 to 3% solids concentration) were prepared using dimethyl formamide or a combination of dimethyl formamide, toluene and isopropanol as the solvent. The desired weight ratios of poly-α-amino acid and progesterone containing about 0.2% of radioactive labelled progesterone-4-$C^{14}$ were mixed into the solvent and films cast therefrom on a Teflon ® surface.

Film implants devices for evaluation were thus formed loaded with 9.09% w/w progesterone using the following copolymers as the matrix material:
  20/80 glutamic acid/leucine
  35/65 glutamic acid/leucine
  40/60 glutamic acid leucine
  40/60 benzyl glutamate/leucine.

In these in vivo evaluations, rats were anesthetized with a solution of chloral hydrate (1.9 g/50 ml; injected 2 ml/100 g body weight) and a small incision was made through the skin on the dorsal surface. Each rat received a film implant, which had been rinsed with Earle's Balanced Salt solution, inserted subcutaneously, and pushed away from the incision area. The incisions were sutured and the animals were placed in individual metabolism cages designed for the collection of urine.

The rats were sacrificed according to a predetermined program and the implants were removed, dissolved in N,N'-dimethyl formamide and assayed to determine the fraction of progesterone remaining.

20/80 Glutamic acid/leucine implants

Typical film dimensions for a series of these implants are given in Table 2.

TABLE 2

Physical Characteristics of 20/80 Glutamic Acid/Leucine Implants

| Rat No. | Film Wt. (mg) | Area (cm$^2$) | Thickness (cm) | Initial Radioactivity (dpm) |
| --- | --- | --- | --- | --- |
| 1 | 8.2 | 2.02 | 0.0076 | 500,000 |
| 2 | 7.1 | 2.94 | 0.0076 | 430,000 |
| 3 | 10.3 | 3.08 | 0.0076 | 630,000 |
| 4 | 16.8 | 4.84 | 0.0076 | 1,030,000 |
| 5 | 11.3 | 1.34 | 0.0381 | 690,000 |
| 6 | 12.6 | 1.70 | 0.0203 | 770,000 |
| 7 | 11.1 | 1.72 | 0.0254 | 680,000 |
| 8 | 11.3 | 1.24 | 0.0305 | 690,000 |

Figure 10:
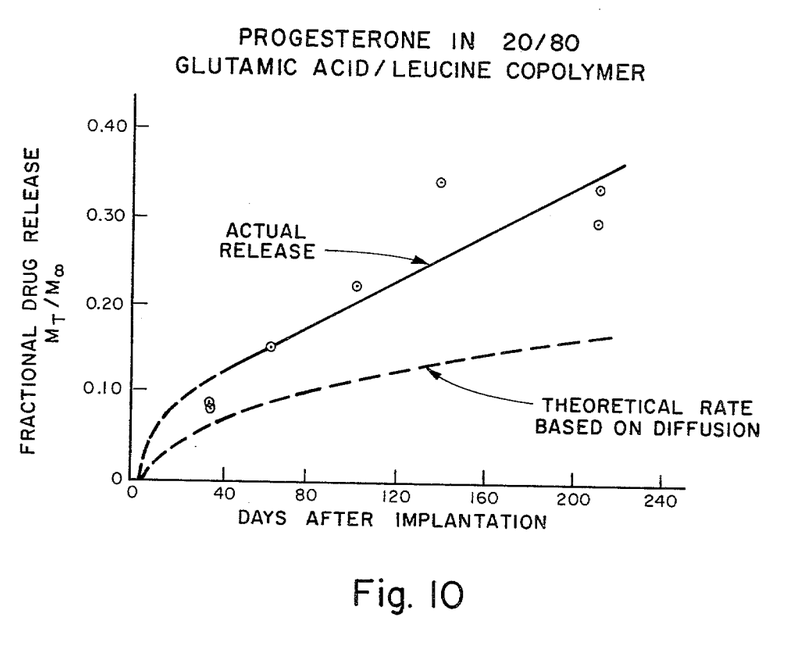
FIG. 10 is a plot of fractional release of progesterone from 20/80 glutamic acid/leucine copolymer implants in in vivo testing in rats.

FIG. 10 is a plot of the actual release of the progesterone over a period of 220 days after implantation. In this plot, the actual drug release was determined as the difference between the initial drug content of the implants and the residual drug found at the time of sacrifice.

If the release of the drug is solely by the mechanism of diffusion then it is possible to calculate the theoretical release over the same period using Fick's first law $$J = - \frac{D d C_p}{dx}$$

where J is the flux in g/cm$^2$/sec., $C_p$ is the concentration of progesterone in the polymer in g/cm$^3$, $dC_p/dx$ is the gradient in concentration and D is the diffusion coefficient of progesterone in the polymer in cm$^2$/sec. The minus sign reflects the fact that the direction of permeation is down the gradient in concentration.

When the drug is homogeneously dissolved in the polymer, as was the case in these implants, Fick's law may be solved to give the following desorption expression:

$$M_t = 1 - \sum_{n=0}^{\infty} \frac{8 \exp(-D[2n+1]^2 \pi^2 t/l)^2}{(2n+1)^2 \pi^2}$$

where $M_\infty$ is the total amount of drug in the polymer, $M_t$ is the amount desorbed at time, t, and l is the thickness of the film.

This equation may be simplified to $$\frac{M_t}{M_\infty} = \left( 4 \frac{Dt}{\pi l^2} \right)^{\frac{1}{2}} \text{ for } 0 \leq \frac{M_t}{M_\infty} \leq 0.6$$

to obtain valid values until 60% of the drug is released.

Using this approach, it is possible to calculate the theoretical release, based on diffusion, of the drug from these implants. These calculations were made and the results are plotted in FIG. 10. Since the actual release of drug from this series of implants was more than twice as fast as that which can be attributed to diffusion alone, it is reasonable to conclude that biodegradation of the glutamic acid/leucine copolymer matrix was responsible for the release of that quantity of drug not attributable to diffusion. Visual examination of the implants removed verified the fact that biodegradation of the polymer had occurred.

The rate of progesterone release from these implants having a matrix of 20/80 glutamic acid/leucine copolymer indicates that this poly-α-amino acid loaded with about 9 to 10%, by total implant weight, of the drug is suitable for the administration of the drug over a dosage range of from about one to ten µg/day for time periods of twelve months or longer.

40/60 Glutamic acid/leucine implants

Six film implants ranging in weight between 3.2 and 7.4 mg and in areas between 1.66 and 2.13 cm$^2$ were made by the process described, implanted into rats and evaluated as outlined above. The progesterone release rates for these 40/60 glutamic acid/leucine implants were more rapid than those of the 20/80 copolymer. The in vivo release rate was approximately 13 µg/cm$^2$/day and was essentially complete within thirty days. The progesterone release from these implants over this short time period was due essentially to diffusion of the drug through the copolymer matrix which appeared to be biocompatible as evidenced by the lack of adverse tissue reaction.

When 35/65 glutamic acid/leucine copolymer was substituted for the 40/60 material, essentially the same release rates were noted. It was also determined that films using the 35/65 copolymer containing 10%, 20% and 40% progesterone by weight were relatively insensitive to drug loading so far as diffusion coefficients were concerned. These implants exhibited average diffusion values ranging from $2.1 \times 10^{-8}$ cm$^2$/hr. to $8.5 \times 10^{-8}$ cm$^2$/hr.

40/60 Benzyl glutamate/leucine implants

The substitution of benzyl glutamate for glutamic acid in the copolymer used to form implants prepared as previously described materially altered the progesterone release rate from the implants. Implants having 9.09% by weight progesterone and ranging in weight between 17.1 and 21.2 mg and in area between 2.13 and 2.78 cm$^2$ were evaluated in rats and found to exhibit a release rate of about 3.5 µg/cm$^2$/day for at least 80 days, at which time less than 45% of the initial drug content was released. In these implants the drug was released by both diffusion and biodegradation. Biocompatibility of these implants was evidenced by the absence of any adverse tissue reaction.

EXAMPLE 3

Copolymers of 40/60 and 35/65 glutamic acid/leucine were prepared as described in Example 2. The polymers were then blended with naltrexone which is a narcotic antagonist drug, and cast into films in the following manner. The polymer was dissolved in dimethylformamide to prepare a 2% solution. Dry crystalline naltrexone (free base) was then added to portions of the polymer solution to prepare casting solutions containing 10%, 20%, and 40% naltrexone based on the total solution weight. The naltrexone was radioactively labelled with tritium in the 15, 16 positions and exhibited an activity of 0.48 mCi/gram. Films were prepared by casting the solutions in a Teflon mold. By alternately casting and drying (at 40°–60° C.) thin layers of the solutions, films 0.007 cm to 0.070 cm were built up. This gradual build-up helps ensure that a relatively homogeneous dispersion of drug in the polymer is produced. The films were placed in a vacuum oven at 50°–70° C., 30 in. Hg, for 24 hours to remove the last traces of solvent. They were then cut to form implant models.

The resulting implants were evaluated by both in vitro and in vivo techniques. In making the in vitro evaluations the films were measured for weight, thickness, and surface area, and were then rinsed briefly with Earle's Balanced Salt Solution (IX—without phenol red, Grand Island Biological Company). Individual films were placed in stoppered test tubes containing 10 ml of the Earle's solution. The tubes were placed in a shaker water bath at 37° C. and were gently agitated. Drug concentration of the solution was periodically assayed by scintillation counting techniques to permit an evaluation of the in vitro drug-release behavior of the copolymers. (The solutions were replaced sufficiently frequently that the naltrexone concentration remained far below saturation, i.e., below ~460 mg/100 ml).

In making the in vivo evaluations, twenty mice (Charles River CD #1), excluding controls, were prepared for containing $^3$H-naltrexone using the following protocol:

| Series | Copolymer | Number Animals Used |
|---|---|---|
| 1 | 40/60, 40% Naltrexone | 4 |
| 2 | 40/60, 20% Naltrexone | 4 |
| 3 | 35/65, 40% Naltrexone | 6 |
| 4 | 35/65, 20% Naltrexone | 6 |

Under pentobarbital Na (60 mg/kg) anesthesia the drug release devices were implanted subcutaneously on the back of a mouse as follows: the area above the incision was shaved and washed with an alcohol-Betadine ® solution. A ¼" incision was made along the middorsal line; then a pocket ½-¾" deep was made in the fascia between skin and muscle with blunt forceps. The implant was grasped in the forceps and pushed into the pocket so that it would remain well removed from the area of the incision. The incision was closed with 4-0 silk. Immediately after surgery, the mice were fitted with coprophagy cups and placed in metabolic cages. The coprophagy cups assured complete separation of urine and feces and thus allowed for an accurate evaluation of the relative magnitudes of excretion by both routes. In those cases where the experiments were carried out over the longer periods of time it became necessary to periodically remove the tail cups and transfer the animals to standard wire cages. These animals were then periodically returned to metabolic cages for 1- or 2-day excretory collection periods during a week.

Finally, the effectiveness of the naltexone released was determined by a Dewey-Harris tail flick test to determine its ability to block the effect of morphine sulfate administered to the mice in dosages of 17.0 mg/kg.

The results of the in vitro evaluation of the implants made with the 40/60 glutamic acid/leucine polymer showed that the cumulative fraction of drug released, $M_t/M_\infty$, as a function of time increased as the thickness of the films decreased and as the initial concentration of drug (i.e., 10%, 20%, or 40%) was raised. The time to release 90% of the naltrexone loading became shorter as the naltrexone content was increased, being in the range of about 50 to 250 hours for the 10% loading, 20 to 90 hours for the 20% loading, and only 18 to 25 hours for the 40% loading. Similar results were obtained from the in vivo testing. These rapid rates of drug release appeared to be attributable to the fact that the polymer exhibited some water-swellability.

The implants formed of 35/65 glutamic acid/leucine copolymer released drug at a rate which depended upon the initial naltrexone loading. However, the duration of release was greatly prolonged at all concentrations when contrasted with the 40/60 copolymer implants. In in vitro testing, those films containing 40% by weight naltrexone were exhausted after 250 hours; those with 20% had released less than 70% in 250 hours; and those with 10% had released less than 20% of their initial drug loading over this same time period. Similar results were obtained from the in vitro tests.

In the tail flick tests, the implants containing 30% naltrexone were found to provide effective blocking of morphine sulfate challenges for 28 days at which time the tests were still underway. These data are summarized in Table 3.

The data of Table 3 clearly show that the drug antagonist, naltrexone, was released over an extended period of time in a form to serve as an effective antagonist to morphine sulfate.

EXAMPLE 4

Glutamic acid/leucine copolymers having 20/80 and 10/90 composition molar ratios were also formed with naltrexone contents of 20% and 40%, and of 40%, respectively. Diffusion coefficients for these implants, as well as those of the implants of Example 3, were determined with the results given in Table 4.

TABLE 3

Model Film Implants
Matrix: 35/65 Glutamic Acid/Leucine
Drug: Naltrexone
Drug Loading: 20%

| Implant Thickness (cm) | Initial Drug Wt. (μg) | Percent Antagonism (Elapsed time, days) | | | | | | | | | | |
|---|---|---|---|---|---|---|---|---|---|---|---|---|
| | | 1 | 4 | 7 | 9 | 11 | 14 | 16 | 18 | 21 | 24 | 28 |
| 0.061 | 580 | | | 100 | | | 100 | | | 100 | 100 | 100 |
| 0.056 | 490 | | 73 | 64 | | 65 | | | 100 | 100 | | 100 |
| 0.048 | 660 | | | 100 | | | 100 | | | 100 | 100 | |
| 0.046 | 405 | 100 | | | 100 | | | 100 | | 100 | 100 | |
| 0.043 | 465 | | 100 | | | 100 | | | 100 | 100 | | 100 |
| 0.043 | 550 | 100 | | | 100 | | | 72 | | 100 | | 100 |

TABLE 4

Diffusion Coefficients for
Glutamic Acid/Leucine-Naltrexone Implants

| Copolymer Composition Glu. Acid/Leu. | Naltrexone Content (Wt. %) | Diffusion Coefficient (cm²/hr.) |
|---|---|---|
| 40/60 | 10 | $20 \times 10^{-7}$ |
|  | 20 | $22 \times 10^{-7}$ |
|  | 40 | $120 \times 10^{-7}$ |
| 35/65 | 10 | $0.31 \times 10^{-7}$ |
|  | 20 | $11.5 \times 10^{-7}$ |
|  | 40 | $26 \times 10^{-7}$ |
| 20/80 | 20 | $1.0 \times 10^{-7}$ |
|  | 40 | $12 \times 10^{-7}$ |
| 10/90 | 40 | $19 \times 10^{-7}$ |

The wide range in naltrexone diffusion coefficients are achievable using glutamic acid/leucine copolymers allows a great deal of flexibility in the design of suitable delivery vehicles. Thus it is possible to provide implant devices capable of releasing a drug at a predetermined rate for a predetermined period of time, e.g., one month, six months, one year, etc.

EXAMPLE 5

Implants were formed into rod configuration containing the drug antagonist naltrexone. The rods, having diameters in the range of 0.4 to 0.8 mm and weighing between 1.9 and 7.5 mg, were formed by extruding the drug-containing copolymer.

Finely ground polymer, prepared as previously described, was dry blended in the desired proportion with naltrexone (tritium labelled). Sufficient solvent (dimethylformamide) was added as a processing aid to make a 50% solids paste. This moldable mass was then placed in a steel compression mold that had a die cavity adapted to accept a screw-in die. Rods were extruded at room temperature by exerting moderate pressure on a plunger. The rods were then dried at 40° C. to remove the solvent.

In an attempt to minimize an initial burst of drug from the rod-shaped implants, they were coated with pure copolymer, using a 2% solution of 20/80 glutamic acid/leucine in a toluene/dimethylformamide (5/1) mixture. When the cumulative fraction of drug released, $M_1/M_\infty$, was plotted versus $t^{\frac{1}{2}}/l$ (where t is time and l is rod diameter) it was found that there occurred a high initial release believed to be due to a high concentration of naltrexone deposited on the exterior of the rods as they were dried to remove solvent. The overcoating, which may not have been hole-free, appeared to be ineffective in preventing this initial burst. For example, in the case of the 35/65 rods containing 20% naltrexone, a high initial diffusion coefficient was found. However, as time passed, the apparent diffusion coefficient decreased to a point where it was comparable to that measured for 35/65 film containing a comparable amount of naltrexone. Consequently, the 35/65 rod-shaped devices appeared to release naltrexone in a manner quite similar to that observed with the films. In the case of the 20/80 rods containing 40% naltrexone, the same general drug releasing behavior was found. Rods which were uncoated showed a very high initial diffusion coefficient and then a gradual reduction. Rods which had received three coats of pure 20/80 copolymer showed a smaller initial burst and a gradual approach to the same steady state diffusion coefficient as the uncoated rods. On the other hand, rods receiving five coats of pure polymer showed a constant diffusion coefficient for the entire experiment.

Thus in the case of rod-configured implants constructed in accordance with this invention, it is possible to predetermine the drug release rate and release period by choice of polymeric matrix, drug loading, and constitution of the implant device including pure polymer coatings.

EXAMPLE 6

Rod-configured implants in the form of closed polymeric tubes containing concentrated drug cores were made. This example presents one exemplary technique for forming these implants.

The tubes were prepared by casting a solution of the polymer onto a rotating glass mandrel. To minimize the possibility of pin hole formation, the tubes were typically built up by casting and drying at least three coatings so that a pin hole in any one layer would be unlikely to line up with any holes in the other layers. However, no evidence was observed of pin holes in tubes prepared from even a single casting. The tubes were then slipped off the mandrel and cut to desired lengths. A naltrexone-copolymer core containing 80% by weight of the drug was then inserted into the tube and pure polymer plugs placed at each end to cap and seal the tubes to form a complete pure polymer casing.

Using pure 35/65 copolymer to form the tubings and end caps and 35/65 copolymer to form a core containing 80% by weight of naltrexone, 6 tube implants were made and implanted in mice. The implants were approximately 1 cm long, had an outside diameter of 1.88 mm, a wall thickness of 0.09 mm and contained from 3.6 to 11.8 mg of drug in the cores.

Figure 11:
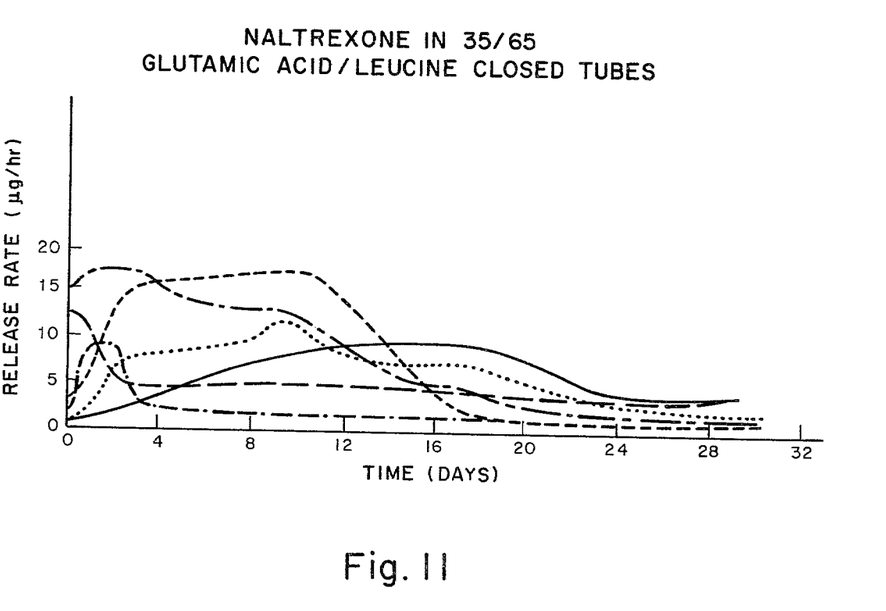
FIG. 11 is a plot of the release rate over a period of 30 days for closed tube implants containing naltrexone when implanted in rats.

These implants were introduced in mice and urinary radioactivity was determined as a measurement of drug release. The actual release rates over a span of about 30 days are plotted for the six individual implants in FIG. 11. Although these implants were too small to deliver sufficient naltrexone to block the effect of morphine sulfate in the mice receiving them as determined by the tail flick test, the data obtained make it possible to calculate the size of a similar tube implant to deliver 210 μg/hr. (5 mg/day) of naltrexone to a human to effectively block morphine sulfate. Assuming that the implant is to release this level of drug for 30 days it must carry a payload of approximately 150 mg of the drug, and this can be accomplished with a tube less than 3 mm in diameter and about 3 cm long (or in multiple tubes with smaller dimensions). Such a tube will exhibit about five times the surface area and consequently five times the release rate of the tubes described above, yielding a release rate of approximately 100 μg/hr, satisfying the human dosage requirements. These calculations show that the tube dosage form is a realistic approach to the development of a suitable delivery vehicle for naltrexone. Moreover, tube implants of these dimensions may be injected by trocar without surgery.

These examples clearly illustrate the fact that the drug delivery devices of this invention offer a great deal of flexibility in release rates, in total release periods, in the drugs which can be delivered and in biodegradation rates. These factors may be predetermined and realized through the choice of the poly-α-amino acid component used, of configuration of the implant device and of drug loading. Throughout the extensive test program so far conducted there has been no evidence of adverse tissue reaction noted from the gross inspection of the animals containing the copolymers used. In general, the implant sites have been found to be nonedematous, nonflamed, and with no excessive vascularization, fibrosis, or encapsulation of the implants. Thus the implants have exhibited good biocompatibility.

It will thus be seen that the objects set forth above, among those made apparent from the preceding description, are efficiently attained and, since certain changes may be made in carrying out the above process and in the article set forth above, among those made apparent from the preceding description, are efficiently attained and, since certain changes may be made in carrying out the above process and in the article set forth without departing from the scope of the invention, it is intended that all matter contained in the above description or shown in the accompanying drawings shall be interpreted as illustrative and not in a limiting sense.

I claim:

1. An implant device for the controllable release of at least one substance into a living host into which it is implanted, comprising
   (a) a substance to be released within a living host; and
   (b) a matrix material prepared from a block copolymer of the formula where $R_1$, $R_2$, $R_3$ and $R_4$ are

$-H$, $-CH_3$, $-CH_2COOH$, $-CH_2CH_2COOH$,

$-CH_2C(CH_3)CH_3$, $-CH_2CH_2CH_2CH_2NH_2$, $-CH_2CH_2SCH_3$, $-CH_2SH$, $-CH_2-$$-CH_2OH$ or and m, n, p and q range between 1 and 100, or a copolymer of two or more α-amino acids distributed at random along the chain of the formula wherein $R_1$ and $R_2$ are defined above, which is biocompatible and biodegradable within the host environment into which it is implanted; does not form covalent bonds with said substance to be released; has an average molecular weight of 20,000 to 1,000,000; and is essentially free of any carrier of said substance, said substance being distributed within said matrix to provide a controlled rate of release for systemic utilization within said host by diffusion, hydrolysis or a combination thereof of said matrix material said implant device being shaped as an injectable configuration.

2. An implant device in accordance with claim 1 wherein said copolymer is formed of γ-benzyl-L-glutamate and L-leucine.

3. An implant device in accordance with claim 1 wherein said copolymer is formed of L-glutamic acid and L-leucine.

4. An implant device in accordance with claim 1 wherein said substance is physically admixed throughout said matrix.

5. An implant device in accordance with claim 1 wherein said implant device contains a plurality of said substances for release in sequence.

6. An implant device in accordance with claim 1 wherein said matrix structure is configured as a rod.

7. An implant device in accordance with claim 6 wherein said rod is formed as a core with at least one layer of said matrix material built up thereon, said core and each layer having a predetermined concentration of said substance distributed therein.

8. An implant device in accordance with claim 6 wherein said rod is formed with an axial opening therethrough, thereby defining an internal surface as well as an external surface.

9. An implant device in accordance with claim 6 wherein said rod is formed as a sealed tube.

10. An implant device in accordance with claim 9 wherein said sealed tube comprises an outer casing formed of said matrix material and an inner core comprising said substance to be released.

11. An implant device in accordance with claim 10 wherein said core is formed of said copolymer acid component having said substance physically admixed therethrough.

12. An implant device in accordance with claim 11 wherein said inner core comprises up to about 90% by weight of said substance.

13. An implant device in accordance with claim 1 wherein said matrix structure is configured as an essentially spherical microcapsule.

14. An implant device in accordance with claim 13 wherein said microcapsule comprises a core with a coating of essentially pure copolymer acid.

15. An implant device in accordance with claim 14 wherein said core is formed of said copolymer acid component having said substance physically admixed therethrough.

16. An implant device in accordance with claim 1 wherein said substance is a drug.

17. An implant device in accordance with claim 16 wherein said drug is a fertility control agent.

18. An implant device in accordance with claim 17 wherein said fertility control agent is progesterone.

19. An implant device in accordance with claim 16 wherein said drug is a narcotic antagonist.

20. An implant device in accordance with claim 19 wherein said narcotic antagonist is naltrexone.

21. A process for delivering at least one substance at a controllable release rate into a living host, comprising implanting into said host an implant device, comprising
   (a) a pharmaceutically effective quantity of a substance to be released within a living host; and (b) a matrix material prepared from a block copolymer of the formula where $R_1$, $R_2$, $R_3$ and $R_4$ are —H, —CH$_3$, —CH$_2$COOH, —CH$_2$CH$_2$COOH, —CH$_2$C(CH$_3$)CH$_3$, —CH$_2$CH$_2$CH$_2$CH$_2$NH$_2$, —CH$_2$CH$_2$SCH$_3$, and m, n, p and q range between 1 and 100, or a copolymer of two or more α-amino acids distributed at random along the chain of the formula wherein $R_1$ and $R_2$ are defined above which is biocompatible and biodegradable within the host environment into which it is implanted; does not form covalent bonds with said substance to be released; has an average molecular weight of 20,000 to 1,000,000; and is essentially free of any carrier for said substance, said substance being distributed within said matrix to provide a controlled rate of release for systemic utilization within said host by diffusion, hydrolysis or a combination thereof of said matrix material, said implant device being shaped as an injectable configuration.

22. A process in accordance with claim 21 wherein said implant device releases a plurality of said substances in sequence.

23. A process in accordance with claim 21 wherein said matrix structure is configured as a rod.

24. A process in accordance with claim 23 wherein said rod is formed as a core with at least one layer of said matrix material built up thereon, said core and each layer having a predetermined concentration of said substance distributed therein.

25. A process in accordance with claim 23 wherein said rod is formed with an axial opening therethrough, thereby defining an internal surface as well as an external surface.

26. A process in accordance with claim 23 wherein said rod is formed as a sealed tube.

27. A process in accordance with claim 26 wherein said sealed tube comprises an outer casing formed of said matrix material and an inner core comprising said substance to be released.

28. A process in accordance with claim 27 wherein said core is formed of said poly-α-amino acid component having said substance physically admixed therethrough.

29. A process in accordance with claim 28 wherein said inner core comprises up to about 90% by weight of said substance.

30. A process in accordance with claim 2 wherein said matrix structure is configured as an essentially spherical microcapsule.

31. A process in accordance with claim 30 wherein said microcapsule comprises a core with a coating of essentially pure copolymer acid.

32. A process in accordance with claim 3 wherein said core is formed of said poly-α-amino acid component having said substance physically admixed therethrough.

33. A process in accordance with claim 2 wherein said substance is a drug.

34. A process in accordance with claim 33 wherein said drug is a fertility control drug.

35. A process in accordance with claim 34 wherein said fertility control drug is progesterone.

36. A process in accordance with claim 33 wherein said drug is a narcotic antagonist.

37. A process in accordance with claim 36 wherein said narcotic antagonist is naltrexone.

38. An implant device in accordance with claim 3 wherein the mole ratio of said L-glutamic acid to said L-leucine ranges between about 10 to 90 and 40 to 60.

* * * * *